(12) United States Patent
Schwartzman et al.

(10) Patent No.: US 6,725,085 B2
(45) Date of Patent: Apr. 20, 2004

(54) METHOD AND APPARATUS FOR CHARACTERIZING CARDIAC TISSUE FROM LOCAL ELECTROGRAMS

(76) Inventors: Armin Schwartzman, 450 Marion Way, Palo Alto, CA (US) 94301; Daniel Reisfeld, 39 R. Walenberg St., Haifa (IL)

(*) Notice: Subject to any disclaimer, the term of this patent is extended or adjusted under 35 U.S.C. 154(b) by 91 days.

(21) Appl. No.: 09/934,476

(22) Filed: Aug. 22, 2001

(65) Prior Publication Data
US 2002/0151808 A1 Oct. 17, 2002

Related U.S. Application Data
(60) Provisional application No. 60/234,494, filed on Sep. 22, 2000.

(51) Int. Cl.[7] ............................................. A61B 5/0402
(52) U.S. Cl. ..................................... 600/509; 600/512
(58) Field of Search ................................ 600/509, 512, 600/518; 607/4, 5, 9

(56) References Cited

U.S. PATENT DOCUMENTS

| | | | |
|---|---|---|---|
| 5,318,037 A | * 6/1994 | Evans et al. ............... 128/696 |
| 5,391,199 A | 2/1995 | Ben-Haim ................. 607/122 |
| 5,409,000 A | 4/1995 | Imran ....................... 600/374 |
| 5,443,489 A | 8/1995 | Ben-Haim ................. 607/115 |
| 5,588,432 A | 12/1996 | Crowley ................... 600/439 |
| 5,819,007 A | * 10/1998 | Elghazzawi ................ 395/51 |
| 5,891,045 A | * 4/1999 | Albrecht et al. ........... 600/509 |
| 5,921,924 A | 7/1999 | Avitall ...................... 600/374 |
| 5,931,835 A | 8/1999 | Mackey .................... 606/34 |
| 5,931,863 A | 8/1999 | Griffin, III et al. ........ 607/122 |
| 5,967,995 A | 10/1999 | Shusterman et al. ...... 600/516 |
| 6,217,525 B1 | * 4/2001 | Medema et al. .......... 600/508 |
| 6,226,542 B1 | 5/2001 | Reisfeld ................... 600/407 |
| 6,324,421 B1 | * 11/2001 | Stadler et al. ............ 600/509 |

FOREIGN PATENT DOCUMENTS

| | | | |
|---|---|---|---|
| WO | WO 94/04938 A1 | 3/1994 | ............ A61B/5/06 |
| WO | WO 96/05768 A1 | 2/1996 | ............ A61B/5/06 |
| WO | WO 96 32897 A1 | 10/1996 | ............ A61B/17/39 |
| WO | WO 97/24983 A2 | 7/1997 | ............ A61B/5/042 |
| WO | WO 98/30144 A1 | 7/1998 | ............ A61B/5/04 |
| WO | WO 99/05971 A1 | 2/1999 | ............ A61B/8/08 |
| WO | WO 99 55226 A1 | 11/1999 | ............ A61B/5/04 |

OTHER PUBLICATIONS

International European Search Report for application No. 01308040.3 dated Aug. 12, 2002.

(List continued on next page.)

*Primary Examiner*—Carl Layno

(57) ABSTRACT

The property of cardiac tissue at a local site, a plurality of sites of in a region of a heart may be characterized based on local electrograms measured at the local site, at a plurality of sites or in the region, respectively. The property may be characterized by normalizing the local electrogram, extracting a feature vector from the normalized electrogram, and classifying the tissue property based on the feature vector. The method of may further include computing a map of the tissue property and treating the tissue based on the resultant map. Apparatus to characterize the property includes a catheter and a processor to normalize the local electrogram, extract the feature vector from the electrogram and classify the tissue based on the feature vector.

53 Claims, 10 Drawing Sheets

OTHER PUBLICATIONS

Blanchett, T. et al., "KLT—Based Quality Controlled Compression of Single–Lead ECG", IEEE Trans. Biomed. Eng., vol. 45, No. 7, 1998, pp. 942–945.

Semnani, R.J. et al., "Applications of Rank–reduction to ECG Analysis", Computers in Cardiology, 25, 1998, pp. 57–60.

Laguna, P. et al., "Model–based Estimation of Cardiovascular Repolarization Features: Ischaemia Detection and PTCA Monitoring", J. Med. Eng. Tech., 22(2), 1998, pp. 64–72.

Lux, R.L., "Karhunen–Loeve Representation of ECG Data", J. Electrocardiology; vol. 25 Suppl. 1992, pp. 195–198.

Garcia, J. et al., "Comparative Study of Local and Karhunen–Loeve–Based ST–T Indexes in Recordings from Human Subjects with Induced Myocardial Ischemia", Computers and Biomedical Research; 31; 1998; pp. 271–292.

Lay, D., "Linear Algebra and its Applications", (2nd Ed.), Addison–Wesley, 1997, Chapter 7.

Press, W. et al., "Numerical Recipes in C", (2nd Ed.), Cambridge University Press, 1992, Chapter 2.6.

U.S. patent application Ser. No. 09/506,766, Biosense, Inc., pending.

U.S. patent application Ser. No. 09/379,540, Biosense, Inc., pending.

U.S. patent application Ser. No. 09/019,453, Biosense, Inc., pending.

* cited by examiner

VECTOR INDEX

METHOD AND APPARATUS FOR CHARACTERIZING CARDIAC TISSUE FROM LOCAL ELECTROGRAMS

This application claims the benefit of U.S. Provisional Application No. 60/234,494 filed Sep. 22, 2000.

FIELD AND BACKGROUND OF THE INVENTION

The present invention is directed to a method and an apparatus for characterizing a property of cardiac tissue, particularly, the ischemic state of cardiac tissue, from local electrograms.

Patients with ischemia frequently are asymptomatic at rest but experience symptoms under stress. A number of techniques currently exist for diagnosing ischemia in cardiac tissue. One such technique is stress electrocardiography (stress EKG), in which the electrocardiogram is measured while the patient is exercising. Other techniques for detecting ischemia include echocardiography and nuclear imaging. Both of these techniques may also be conducted while the patient is under stress, which may be either induced physically or pharmacologically with agents such as dubotamine. A technique for diagnosing chronic ischemia in patients purely from local electrograms taken when the patient is at rest has not heretofore existed. Furthermore, while some of the above-mentioned techniques can be used to diagnose ischemia at the regional level, they do not reveal ischemia with pinpoint accuracy.

U.S. Pat. No. 5,967,995 discloses a method for predicting life-threatening cardiac arrhythmias by gathering electrocardiographic data, mathematically decomposing the signal into several elements or components that contain the most significant information and tracking the changes in the several elements. The method of the '995 patent does not permit evaluation and diagnosis of a patient without time-dependent historical data. Furthermore the '995 patent does not teach or suggest the possibility of diagnosing the local ischemic state of tissue from local electrograms.

SUMMARY OF THE INVENTION

One aspect of the invention is directed to a method of characterizing a property of cardiac tissue at a local site of a heart based on a local electrogram measured at that local site. The method first involves normalizing the local electrogram. A feature vector is then extracted from the normalized electrogram. The property of the cardiac tissue at the local site is classified based on the resultant feature vector.

Another embodiment of the method of the invention is directed to characterizing a property of cardiac tissue at a plurality of local sites of a heart based on a plurality of local electrograms. This embodiment of the invention first involves normalizing the local electrograms. Feature vectors are then extracted from the normalized local electrograms. The property of the cardiac tissue at the plurality of local sites is then classified based on the extracted feature vectors.

Another embodiment of the method of the invention is directed to characterizing a property of a region of cardiac tissue of a heart based on a plurality of local electrograms measured in the region. This embodiment first involves normalizing the electrograms. An electrogram which is representative of the tissue in the region is then computed from the normalized electrograms. A representative feature vector is then extracted from the representative electrogram. The property of the cardiac tissue in the region is then classified based on the representative feature vector.

Normalizing the local electrograms includes annotating the electrograms, selecting a single cardiac cycle from the electrogram, and representing the cardiac cycle of the electrogram as a vector such that the annotation is at a fixed position within the vector.

In some embodiments, the normalizing step further includes the step of scaling the electrogram. In this case, the electrogram is scaled so as to have a fixed value at a particular feature of the electrogram. The particular feature according to some embodiments corresponds to the annotation.

In some embodiments, the normalizing step further includes the step of centering the electrogram. The normalization step may also include rejecting outlying electrograms.

In some embodiments of the invention, the feature vector is a projection of the normalized electrogram onto a pre-computed subspace. The subspace may be computed by principal component analysis of a training set of electrograms. In this embodiment, the classifying step of the method of the invention is based on the location of the feature vector in the subspace.

In some embodiments, the property being characterized by the method of the invention is indicative of the anatomy of the local site or region. In other embodiments, the property is indicative of a pathological state of the cardiac tissue such as the degree of ischemia of the tissue at the local site or region.

Where the method of the invention involves characterizing the cardiac tissue at a plurality of sites or regions within a chamber of the heart, the method may further include the step of constructing a map of the property of the heart chamber.

In some embodiments, the method of the invention further includes the step of delivering treatment to the tissue at the local site or region. In such cases, the method may further include follow-up characterization of the tissue property to determine the effectiveness of the treatment.

In some embodiments, the local electrograms are measured with an electrode on a catheter. The catheter further comprises a position sensor such as an electromagnetic sensor for measuring the three-dimensional position of the electrode during measurement of the electrogram.

Another aspect of the invention is directed to apparatus for characterizing a property of cardiac tissue at a local site of a heart based on a local electrogram measured at the site. The apparatus of the invention includes a catheter and a processor. The processor performs the functions of normalizing the electrogram, extracting a feature vector from the normalized electrogram, and classifying the property of the cardiac tissue at the local site based on the feature vector. The processor may further perform the function of computing a map of the property of the heart tissue.

In some embodiments of the apparatus of the invention, the catheter, which includes an electrode for measuring the local electrogram, further includes a position sensor such as an electromagnetic sensor for measuring the three-dimensional position of the electrode during measurement of the electrogram.

The apparatus of the invention may further include means for delivering treatment to the tissue.

The present invention will be more fully understood from the following detailed description of preferred embodiments, taken together with the following drawings in which:

DETAILED DESCRIPTION OF PREFERRED EMBODIMENTS

The present invention is directed to methods and apparatus for characterizing a property of cardiac tissue from local cardiac electrograms. In its various embodiments, the method of the invention is useful for characterizing the property of tissue at a local site, at a region, or at a plurality of sites in a heart.

As used herein, the term "property" refers to an attribute of the cardiac tissue. Illustrative attributes or properties include, for example, anatomical properties and physiological properties. For example, an anatomical property refers to the location of the site within the heart, for example, in a ventricle or an atrium. It may also refer to other anatomical landmarks, for example, the septum, apex and base of the heart chamber. A physiological property of the site may characterize the presence, absence or extent of pathology, particularly, the degree of ischemia at the site. The method and apparatus of the invention are particularly directed at differentiating the various ischemic stages of tissue such as stunned, hibernating, ischemia at stress and ischemia at rest, in order to enable the physician to design a treatment strategy appropriate for the disease state of the tissue. As used herein, the term "region" refers to a continuous segment of cardiac tissue.

In practicing the method of the invention, the properties of cardiac tissue are characterized based on local electrograms. In contrast to body surface electrograms which measure the electrical activity of the heart using electrodes placed on the surface of the body, the local electrograms used in the method of the invention are acquired by electrodes that are either contacting or are in close proximity to cardiac tissue. The electrograms may be acquired either endocardially (from within the heart) or epicardially (from the outer surface of the heart).

Figure 1:
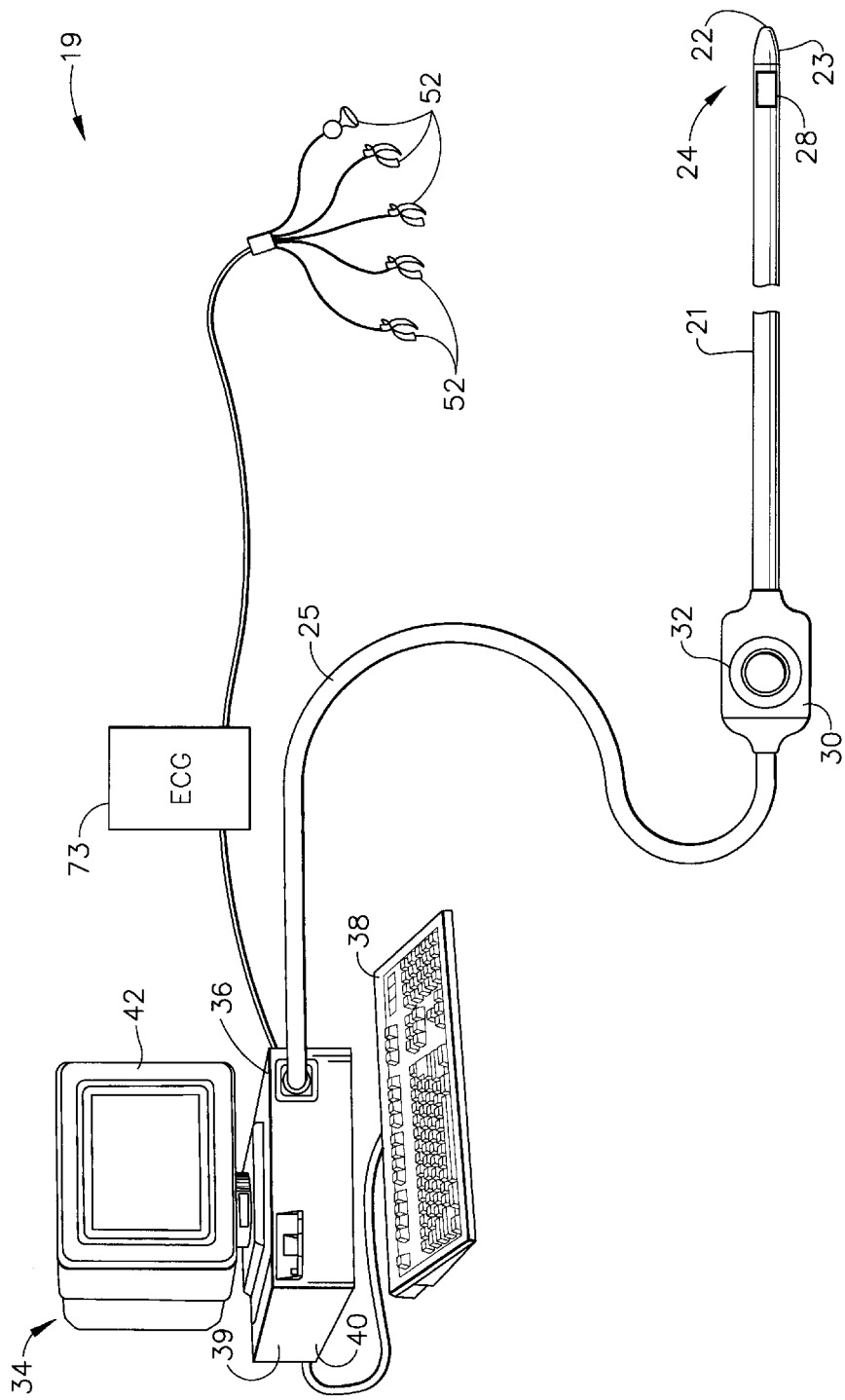
FIG. 1 is a schematic drawing of a catheter system useful for acquiring local endocardial electrograms.
Figure 2:
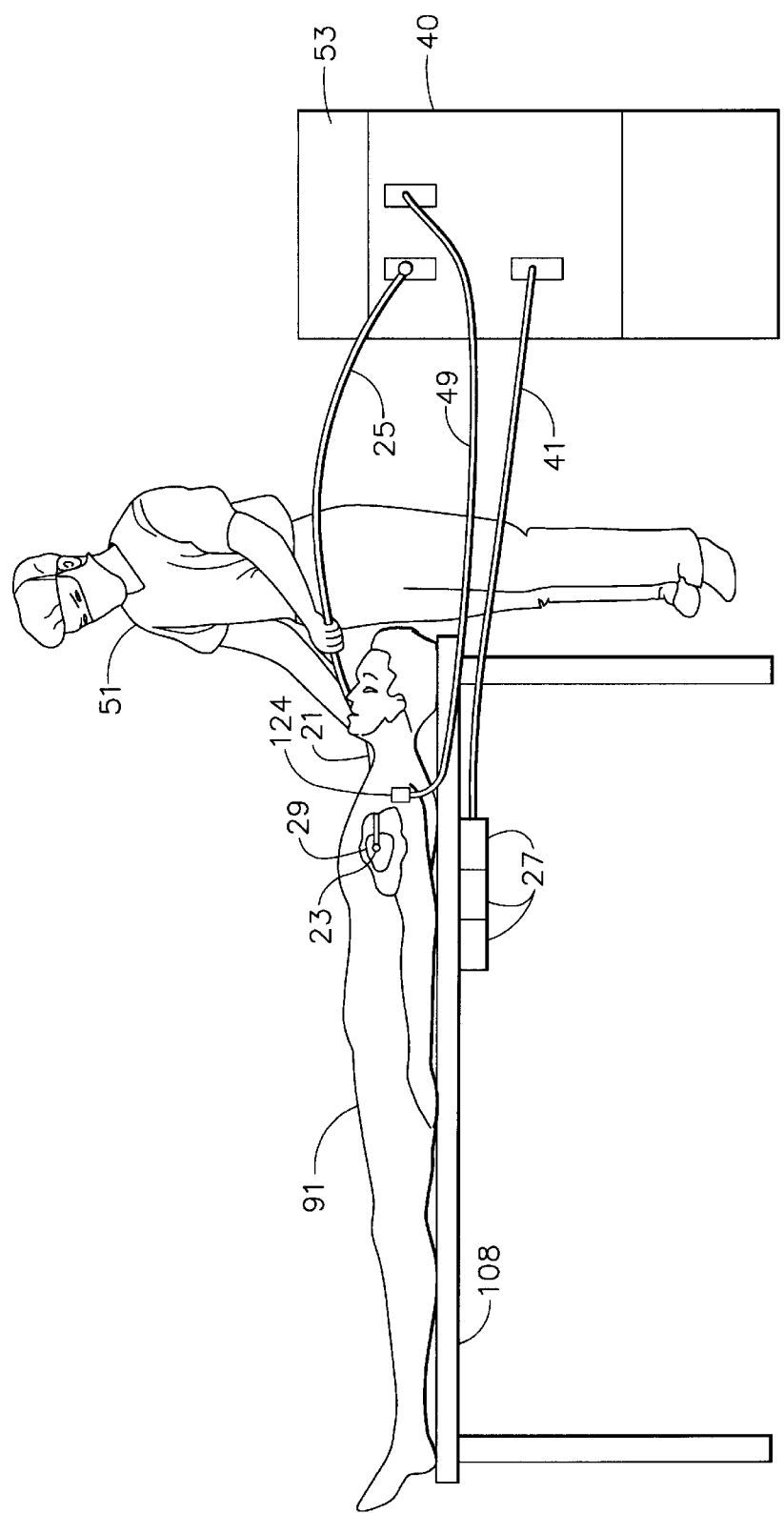
FIG. 2 is a schematic drawing showing additional elements of the catheter system of FIG. 1.

FIG. 1 and FIG. 2 show elements of an illustrative catheter system useful for acquiring local electrograms endocardially for use in the method of the invention. The apparatus includes catheter 21 for intravascular insertion into the human body. Distal end 24 of catheter 21 includes electrode 23 adjacent to catheter distal tip 22 for recording intracardial electrograms, as described, for example, in U.S. Pat. No. 5,391,199 or in PCT application WO97/24983, which are incorporated herein by reference. Alternatively or additionally, distal end 24 of catheter 21 may also include other diagnostic apparatus for recording parameter values at points within the body, and may also include therapeutic apparatus as known in the art.

Catheter 21, used in the apparatus of the invention for acquiring electrograms for use in the method of the invention, may have more than one electrode 23 contained therein. Catheters containing multiple electrodes are described, for example in U.S. Pat. Nos. 5,409,000; 5,588,432; 5,931,863; 5,931,835; and 5,921,924, and in U.S. patent application Ser. No. 09/506,766 which are hereby incorporated herein in their entirety by reference. The use of multi-electrode catheters in collecting electrograms for use in the method and apparatus of the invention permit the simultaneous measurement of electrograms at multiple points in the heart chamber, which can potentially decrease the time required for collecting electrograms at a plurality of sites within the heart.

As shown in FIG. 2, a local electrogram is acquired by advancing catheter 21 having electrode 23 at its distal tip 22 to a point in the heart, preferably contacting the tissue at that point with electrode 23 contained at the catheter distal tip 22, whereupon the electrogram is acquired over some time period. Typically, the local electrograms at each point are acquired as a function of time for a period of several cardiac cycles. The data are then stored in computer memory for future use, as described hereinbelow.

In the embodiment illustrated in FIG. 1, catheter distal end 22 includes a position sensor 28 that generates signals used to determine the position, and, in some embodiments, the orientation of the catheter within the body. Position sensor 28 is preferably adjacent to electrode 23 in a fixed relation with tip 22. In one embodiment, position sensor 28 comprises three coils, such as described in PCT application WO96/05768, which is incorporated herein in its entirety by reference. The position sensor 28 enables continuous generation of up to six dimensions of position and orientation information with respect to externally applied magnetic fields. Alternatively, position sensor 28 may comprise other position and/or coordinate sensors as described in U.S. Pat. Nos. 5,391,199, 5,443,489 and in PCT application WO94/04938, which are incorporated herein by reference. Measurement of the catheter distal tip 22 position during measurement of electrograms from electrode 23 facilitate the computation of a map of the property of the cardiac tissue according to some embodiments of the present invention. By way of example, the NAVI-STAR™ catheter, available from Biosense-Webster, Inc. of Diamond Bar, Calif., is a catheter having both an electrode and a position sensor that may be useful in recording electrograms for use in practicing the present invention. Further, tip 22 may be coated with an opaque marking material to visualize the tip under an imaging apparatus such as a fluoroscope.

The three-dimensional coordinates of the position sensor 28 are typically determined relative to the position of a reference sensor 124 (FIG. 2). The reference sensor 124 is also preferably an electromagnetic sensor that operates according to the same principles as the position sensor 28 in the mapping catheter 21. The reference sensor 124 may be positioned external to the patient, for example, as part of an adhesive patch applied to the patient's skin as shown in FIG. 2. Alternatively, the reference sensor 124 may be positioned internal to the patient, for example, as a component of a reference catheter that is positioned at a particular point in the heart of the patient during the mapping procedure. Thus, the position sensor 28 in the mapping catheter 21 provides the three-dimensional coordinates of the mapping catheter tip 22 relative to the reference position sensor 124.

In constructing a map of the property of the heart, the coordinates of the catheter tip 22 during electrogram acquisition are typically referenced to a particular point in the cardiac cycle, for example, to the end diastole portion of the cardiac cycle, which may be determined from body-surface electrograms.

Catheter 21 preferably includes a handle 30, having controls 32 that are used to steer distal end 24 of catheter 21 in a desired direction. Catheter 21 preferably comprises a steering mechanism in distal end 24 as is known in the art to facilitate repositioning of tip 22.

Catheter 21 is coupled via an extension cable 25 to a console 34 which enables the user to observe and regulate the function of catheter 21. Console 34 preferably includes a computer 36, keyboard 38, signal-processing circuitry 40, which are typically inside computer 36, and display 42. Signal processing circuits 40 typically receive, amplify, filter and digitize signals from catheter 21, including signals from position sensor 28 and electrode 23, whereupon these digitized signals are used by computer 36 to process the electrograms and to compute the position and/or orientation of catheter tip 22. Alternatively, appropriate circuitry may be associated with catheter 21 itself so that circuits 40 receive signals that are already amplified, filtered and/or digitized. Computer 36 also contains a processor 39 for normalizing the local electrograms acquired via electrode 23 of catheter 21. Processor 39 also performs the function of extracting a feature vector from the normalized electrograms and also functions to classify the cardiac tissue based on the feature vectors. Preferably, computer 36 includes a memory for storing position and electrogram information. Processor 39 in computer 36 also functions to compute a map of the property of the cardiac tissue. In some embodiments, computer 36 further comprises dedicated graphics circuitry for displaying the map of the heart property. The computer 36 shown in FIG. 1 is also equipped to receive body surface ECG signals from ECG monitor 73 that is connected to a plurality of ECG body surface leads 52. Alternatively, ECG monitoring may also be conducted directly by signal processing circuits 40.

As shown in FIG. 2, a physician 51 inserts catheter 21 through an incision in the vasculature, e.g., using an intravascular approach, into a chamber of a heart 29 of a patient 91, so that electrode 23 of catheter distal tip 22 and position sensor 28 are inside the heart chamber. In accordance with an exemplary position sensor described in PCT patent application number WO 96/05768, filed Jan. 24, 1995, and in U.S. Pat. No. 5,391,199, which are assigned to the assignee of the present application and whose disclosures are incorporated herein in their entirety by reference, sensor 28 generates signals in response to externally applied magnetic fields generated by electromagnetic field generator coils 27 fixed to operating table 108 in proximity to patient 91. The magnitude of the signals generated by sensor 28 depends on the position and orientation of the sensor in the applied magnetic field. Field generator coils 27 are connected via cable 41 to driver circuits which are part of signal processing circuits 40. Circuits 40 control the operation of the generator coils 27 and the overall position sensor location system.

Alternatively, the catheter system for obtaining local electrograms for use in the present invention may employ field generator coils in the catheter and sensors external to the patient.

While the catheter system has been described herein with reference to electromagnetic position sensors, any other sensor that provides three-dimensional position information and, optionally, orientation information, may be used in obtaining the electrograms for practice of the method of the present invention. Illustrative sensors that are also useful include acoustic sensors and magnetic sensors. For example, acoustic sensors of the type disclosed in U.S. Pat. No. 5,409,000 and in PCT application WO 99/05971, the disclosures of which are incorporated herein in their entirety by reference, may be used in the catheter system to obtain the electrograms for use in the method of the invention.

As disclosed in U.S. Pat. No. 5,391,199, mapping a property of the heart is performed by positioning the distal tip 22 of catheter 21 at a site within the heart, sensing location and electrical information at the site, processing the sensed location and electrical information at the site to create a data point, and repeating these steps a sufficient number of times to create a map of the property of the heart. For an accurate map of the property based on chamber electrical activity, location and electrical data are preferably sensed when electrode 23 at distal tip 22 of catheter 21 is in contact with or in close proximity to the cardiac wall at each site.

Having identified a pathological condition from the electrograms or from the resultant property map of the heart tissue, the physiological condition may be treated by delivering a treatment to the physiologically affected site or sites. One method of treatment involves local ablation of the cardiac surface. As shown in FIG. 2, ablation may be performed by supplying RF energy to a local site from ablation power source 53 via circuits 40 and cable 25 to electrode 23 contained at distal tip 22 of catheter 21. Alternatively, therapeutics may be delivered to the site of a lesion using a delivery catheter that has position sensing capability as described, for example, in co-pending U.S. patent applications Ser. Nos. 09/19,453 and 09/379,540, the disclosures of which are hereby incorporated herein by reference. U.S. patent application Ser. No. 09/19,453 discloses treatments for ischemia that include growth factors such as fibroblast growth factor and vascular endothelial growth factor as well as genes encoding the growth factor. U.S. patent application Ser. No. 09/379,540 discloses delivering cells such as myoblasts or myocytes to the heart for treatment of ischemia. Alternatively, as disclosed in published PCT application 98/30144, the disclosure of which is incorporated herein by reference, the treatment may involve exposing the heart tissue to laser irradiation to promote revascularization of the heart tissue.

In addition, the method and apparatus of the invention are useful for conducting follow-up studies of the property of cardiac tissue to determine the efficacy of a particular treatment protocol.

In another embodiment, the method of the invention is directed to characterizing the property of the cardiac tissue at a plurality of sites. In this case, after acquiring the local electrogram at the first site, the catheter distal tip 24 is advanced to another site within the heart and electrograms are again acquired as described above. This process is repeated until all desired sites are visited with electrode 23 at catheter distal tip 22.

Figure 3A:
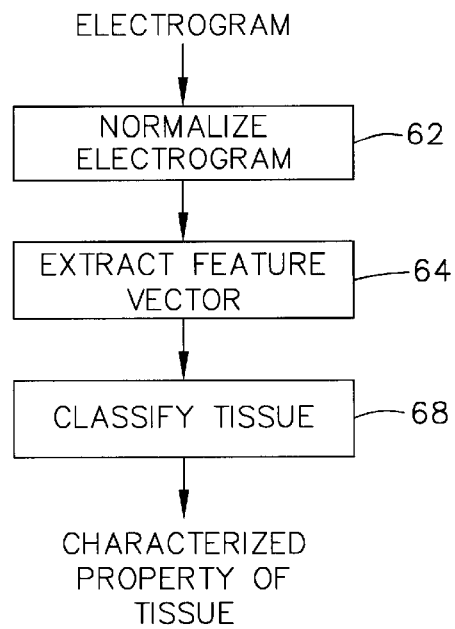
FIG. 3A is a block flow diagram depicting one embodiment of the method of the invention.

As shown in FIG. 3A, the method of the invention of characterizing a property of cardiac tissue at a local site based on an electrogram measured at the local site comprises the steps of normalizing the local electrogram 62, extracting a feature vector from the normalized electrogram 64, and classifying the property of the cardiac tissue based on the feature vector 68.

Normalizing the Electrogram

Figure 3B:
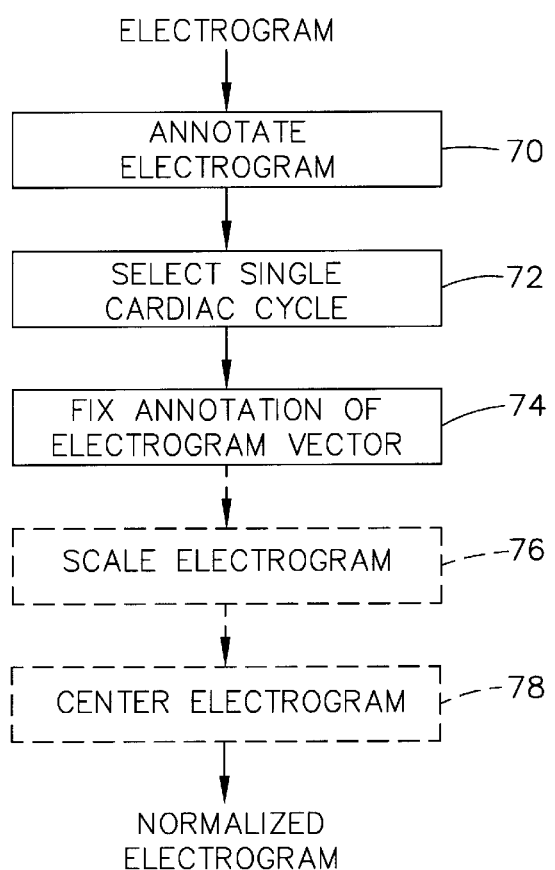
FIG. 3B is a block flow diagram depicting in greater detail the normalizing step of the method of the invention of FIG. 3A.

As shown in FIG. 3B, the step of normalizing the electrogram itself comprises the following three steps: annotating the electrogram 70, selecting a single cardiac cycle from the electrogram 72, and fixing the position of the annotation within the electrogram vector 74. In addition, the step of normalizing the electrogram may include the optional steps of scaling the electrogram 76 and centering the electrogram 78. These steps are described more completely below.

Annotating the Electrogram

Figure 4A:
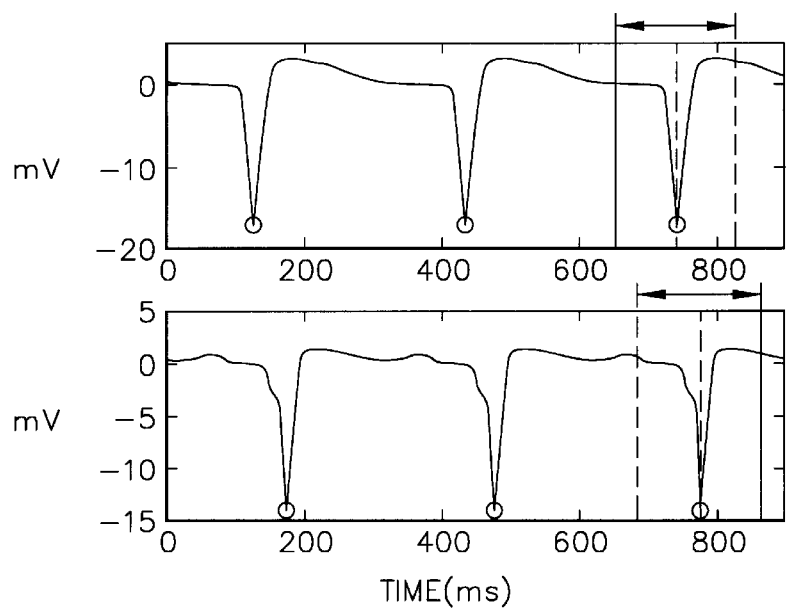
FIG. 4A depicts two annotated local electrograms taken at different sites in an animal heart.

Annotation refers to identifying a particular feature in the recorded electrograms. The annotation feature can be any feature of the electrogram, such as the minimum value, the maximum value, the position of minimum slope or the position of maximum slope, etc. FIG. 4A shows two electrograms taken from different sites of a dog's heart. The electrograms of FIG. 4A are annotated on their minimum value, as indicated by circles on the electrograms of FIG. 4A. The purpose of annotating the electrograms is to use the annotation as a point around which all of the electrograms used in the study are synchronized.

Selecting a Single Cardiac Cycle

The local electrograms are typically recorded at each site for a minimum period of time, for example, about three seconds, at a sampling rate of 1 KHz. Thus, for the human heart, each recorded electrogram records several cardiac cycles. Since the morphology of the electrograms may change from cycle to cycle for a variety of reasons (e.g. arrhythmias, catheter instability, noise), electrograms that do not exhibit an acceptable degree of periodicity are rejected. The recorded electrograms are parsed into cycles according to the cycle length of the simultaneously recorded body surface electrogram. The last segment, which corresponds to the last recorded cycle, is then compared to all of the previous cycles. If the correlation of all cycles in an electrogram is greater than a minimum threshold value, then the last cycle is selected, accepted and stored in computer memory in order to be used in the next step of the method. The minimum correlation between cycles is preferably greater than or equal to about 90%, and is more preferably greater than or equal to about 95%.

Fixing Annotation of Electrogram Vector

As will be explained herein, in some embodiments, the method of the invention requires the use of a plurality of electrograms; i.e., at least one test electrogram and a number of training electrograms. The purpose of fixing the annotation of the electrogram vector is, in part, to synchronize the at least one test electrogram with the training electrograms.

In other embodiments, the invention is applied to characterizing the property of the tissue at a plurality of sites based on a plurality of local electrograms. Since different locations within the heart are activated at different times, it is necessary to synchronize all of the electrograms used in the study. The electrograms are shifted in time so that a particular feature of the electrogram, i.e., the annotation, is made to coincide in all the electrograms.

The vector index of the synchronization point is regarded as zero and a window of L1 milliseconds (ms) before (inclusive of zero) and L2 milliseconds after the synchronization point are saved and used in the subsequent analysis. If x(t) is the vector representation of the last beat of a recorded electrogram, then the vector representation of the synchronized electrogram $x^s(t)$ is given by:

$$x^s(t) = x(t + t_0),$$
$$t = -L1, \ldots, L2,$$
$$t_0 = \arg\{\min_t [x(t)]\}$$

Recommended values of L1 and L2 for human hearts are 50 ms and 150 ms, respectively if the annotation is chosen at the minimum value of the electrogram.

Figure 4B:
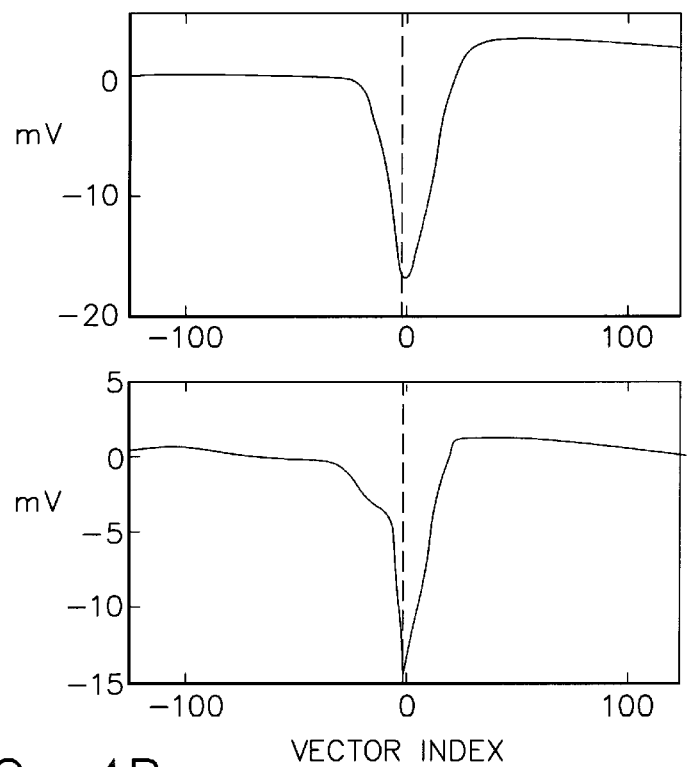
FIG. 4B depicts the last cycle of the electrograms of FIG. 4A in which the electrograms are synchronized around the annotation feature.

FIG. 4B shows the last cardiac cycle from the electrograms of FIG. 4A synchronized around the annotation feature, the minimum electrogram value.

Scaling the Electrogram

In order to emphasize the distinction between electrograms due to differences in signal morphology, differences in amplitude may be compensated for by scaling all of the electrograms so that their values at a particular feature of the electrogram are all equal. The electrograms may be scaled on the annotation feature described above. Alternatively, the electrograms may be scaled on some feature other than the annotation feature.

Assuming that the electrograms are scaled about the annotation feature, if $X_n^s(t)$ represents a synchronized electrogram out of N electrograms, then the scaled electrogram $x_n^{sc}(t)$ may be given by the expression:

$$x_n^{sc}(t) = \frac{1}{a_n} x_n^s(t), t = -L1, \ldots, L2, n = 1, \ldots, N$$

where $\alpha_n$, a scaling factor, and $\bar{x}^s(t)$, the average value of all of the N electrograms at the scaling feature, are given by the expressions:

$$a_n = \frac{x_n^s(0)}{\bar{x}^s(0)}, \bar{x}^s(t) = \frac{1}{N} \sum_{n=1}^{N} x_n^s(t)$$

Figure 5A:
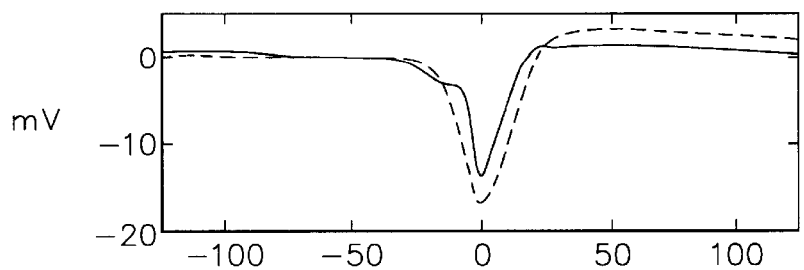
FIG. 5A shows a single local electrogram synchronized with the average of a plurality of local electrograms taken in an animal heart.
Figure 5B:
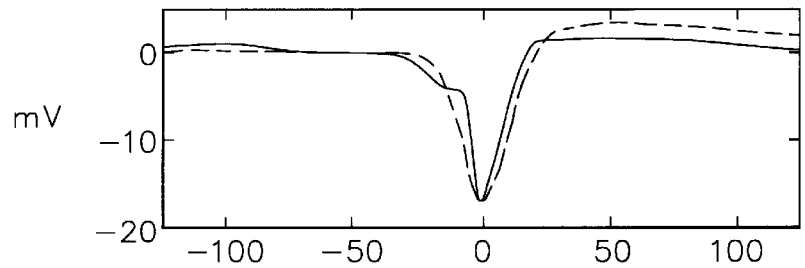
FIG. 5B shows the single electrogram of FIG. 5A scaled with the average electrogram.

FIG. 5A shows a single local electrogram (solid curve) compared to the average of a plurality of local electrograms (dashed curve) taken in a dog heart. FIG. 5B shows the single local electrogram (solid curve) of FIG. 5A scaled with the average electrogram (dashed curve) of FIG. 5A about the annotation feature, the minimum voltage.

Centering the Electrograms

In some embodiments of the method of the invention, a feature vector is extracted from the electrograms in which the feature vector is a projection of the normalized electrogram on a pre-computed subspace. The subspace, in some embodiments, is computed by principal component analysis of a training set of electrograms. When using principal component analysis, the average of all the synchronized electrograms is desirably subtracted from each electrogram. We term this processing "centering" the electrogram. Thus, if $x_n^s(t)$ represents a synchronized electrogram out of N electrograms, then the centered (average-removed) electrogram $x_n^c(t)$ is given by:

$$x_n^c(t) = x_n^s(t) - \bar{x}^s(t), t = -L1, \ldots, L2, n = 1, \ldots, N$$

where $\bar{x}^s(t)$ is as hereinbefore defined.

The electrograms may be both scaled and centered in the method of the invention. In this case, the scaled, centered electrogram, $x_n^{scc}(t)$, is given by the expression:

$$x_n^{scc}(t) = \frac{1}{a_n} x_n^s(t) - \bar{x}^s(t), t = -L1, \ldots, L2, n = 1, \ldots, N$$

wherein $x_n^s(t)$, $\alpha_n$, and $\bar{x}^s(t)$ are as hereinbefore defined.

Figure 5C:
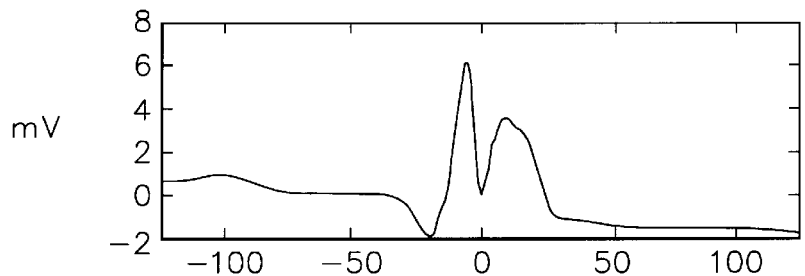
FIG. 5C shows the centered electrogram of FIG. 5B.

FIG. 5C shows the centered, scaled, synchronized electrograms of FIG. 5A and FIG. 5B.

Extracting a Feature Vector from the Normalized Electrogram

As shown in FIG. 3A, the next step in the method of the invention is extracting a feature vector from the normalized electrogram 64. The method of the invention is based on the assumption that individual electrograms may be represented as being composed of basic elements (referred as $u_m$, m=1, . . . , M, below). Having identified these elements (as described in "Training," below), we may calculate components, i.e., coefficients, which represent the extent to which each of the basic elements contributes to a given electrogram.

Let $X_{L \times N} = [x_1, \ldots, x_N]$ be a collection of N synchronized, scaled and centered electrograms recorded at a plurality of sites in a heart, each being an L-dimensional column vector:

$$x_n = [x_n^{scc}(t)], t = -L1, \ldots L2$$

A vector basis of size M $U_{L \times M} = [u_1, \ldots, u_M]$ is a unitary matrix, which is a collection of M fixed column vectors wherein $u_m = [u_m(t)], t = -L1, \ldots, L2$. This vector basis is used as a matrix transformation applied to the data matrix $X_{L \times N}$, as follows:

$$Y = U^T X$$

In the matrix $Y_{M \times N} = [y_1, \ldots, y_N]$ obtained from the above operation, the column $y_n = [y_{1,n}, \ldots, y_{M,n}]^T$ is a feature vector which is a component representation of the electrogram $x_n$. Each of the M components, $y_{m,n}$, of each of the electrograms is computed, within the matrix transformation, as:

$$y_{m,n} = u_m^T x_n = \sum_{t=1}^{L} u_m(t) x_n(t)$$

The components $y_{m,n}$ represent the contribution of each of the basis set vectors $u_m$ to each of the electrograms $x_n$.

If the matrix U is unitary (all of the $u_m$'s are mutually orthogonal), the components $y_{m,n}$ belonging to a particular electrogram $x_n$ are uncorrelated. This means that every component contains information that cannot be obtained from the other components.

Figure 5D:
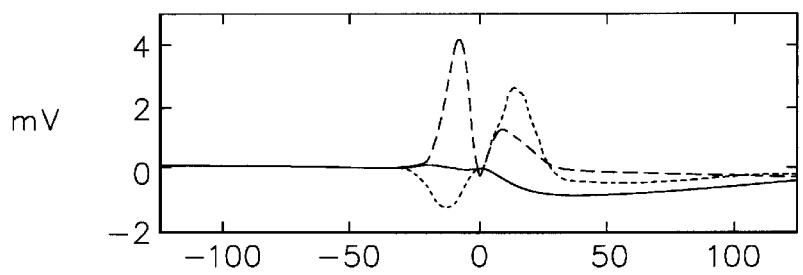
FIG. 5D shows the first three vector basis elements corresponding to the centered, scaled, synchronized electrogram of FIG. 5C.
Figure 5E:
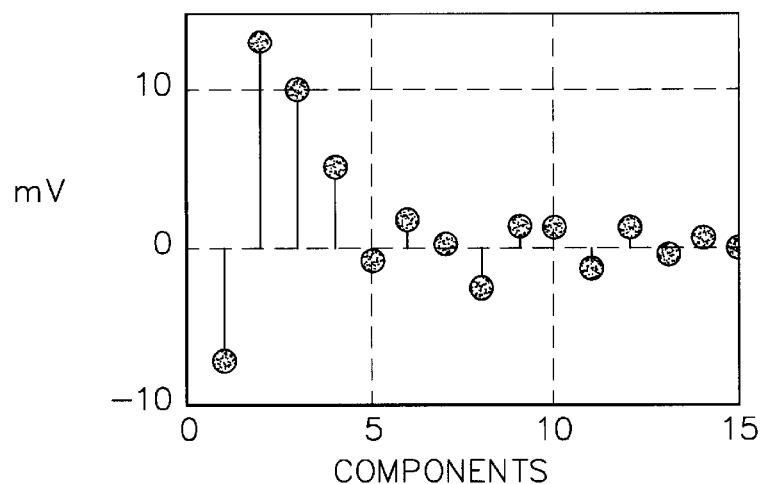
FIG. 5E is a graphical depiction of the first 15 components of the feature vector corresponding to the scaled, centered, synchronized electrogram of FIG. 5C.

FIG. 5D depicts the first three vector basis elements, $u_m$, corresponding to the centered, scaled, synchronized electrogram of FIG. 5C. The matrix elements in FIG. 5D are scaled according to their components, and were computed as described herein. FIG. 5E is a graphical depiction of the first 15 components of the feature vector corresponding to the scaled, centered, synchronized electrogram of FIG. 5C. As can be seen from FIG. 5E, the majority of the variation in the electrogram may be accounted for by the first few components of the feature vector.

Classifying Tissue Property Based on Feature Vector

The next step in the method of the invention is classifying the tissue property at the local site based on the feature vector 68. Tissue at which an electrogram is sampled may be classified according to any of a number of properties. These properties may reflect, for example, the pathology of the tissue at which the electrogram was acquired. Alternatively, the property may be reflective of the location in the heart of the tissue in which the electrogram was acquired. Given the particular property by which the tissue is to be classified, there exists a set of fixed coefficients $\alpha_m$, m=1, . . . ,M, determined as described in "Training" below, which determines the contribution of each component to that particular property. The components $y_{m,n}$ may be linearly combined using the coefficients $\alpha_m$ to form a characteristic parameter $\psi$ defined as follows:

$$\varphi(n) = \sum_{m=1}^{M} \alpha_m y_{m,n}, n = 1, \ldots, N$$

Electrograms are classified by comparing the value of $\psi$ to a predetermined threshold that depends on the characterized property.

The $\alpha_m$ coefficients may be interpreted as components of a classification vector $\alpha = [\alpha_1, \ldots, \alpha_P]^T$ in the subspace determined by U. The characteristic parameter $\psi$ is therefore proportional to the projection of the feature vector y onto the classification vector. Setting a classification threshold for the value of $\psi$ is equivalent to dividing the subspace U into two regions: one for which the projection of the feature vector on the classification vector is greater than the threshold and other for which the projection is smaller than the threshold. Thus, feature vectors are in essence classified according to their position in the subspace U.

Alternatively, the characteristic parameter $\psi$ may be defined as a non-linear combination of the components $y_{m,n}$, where, in the above expression, the components are elevated to powers. Additionally, it is possible to define the characteristic function as a product or ratio of specific components and powers thereof Training Obtain Vector Basis As previously indicated, the method of characterizing cardiac tissue of the invention utilizes a matrix basis of elements and coefficients determined from training. The purpose of training is to (1) obtain the vector basis $U_{L \times M} = [u_1, \ldots, u_M]$, defined previously as a unitary matrix consisting of a collection of M fixed column vectors $u_m = [u_m(t)]$, t=-L1, . . . , L2, and (2) to obtain the set of characteristic coefficients which correlate the vector basis with a particular property of cardiac tissue to be determined.

Figure 3C:
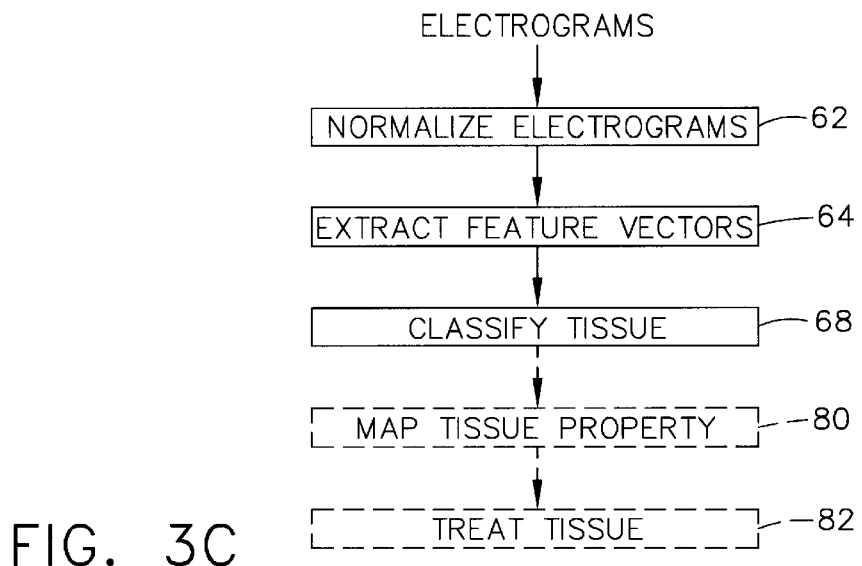
FIG. 3C is a block flow diagram of another embodiment of the method of the invention.
Figure 3D:
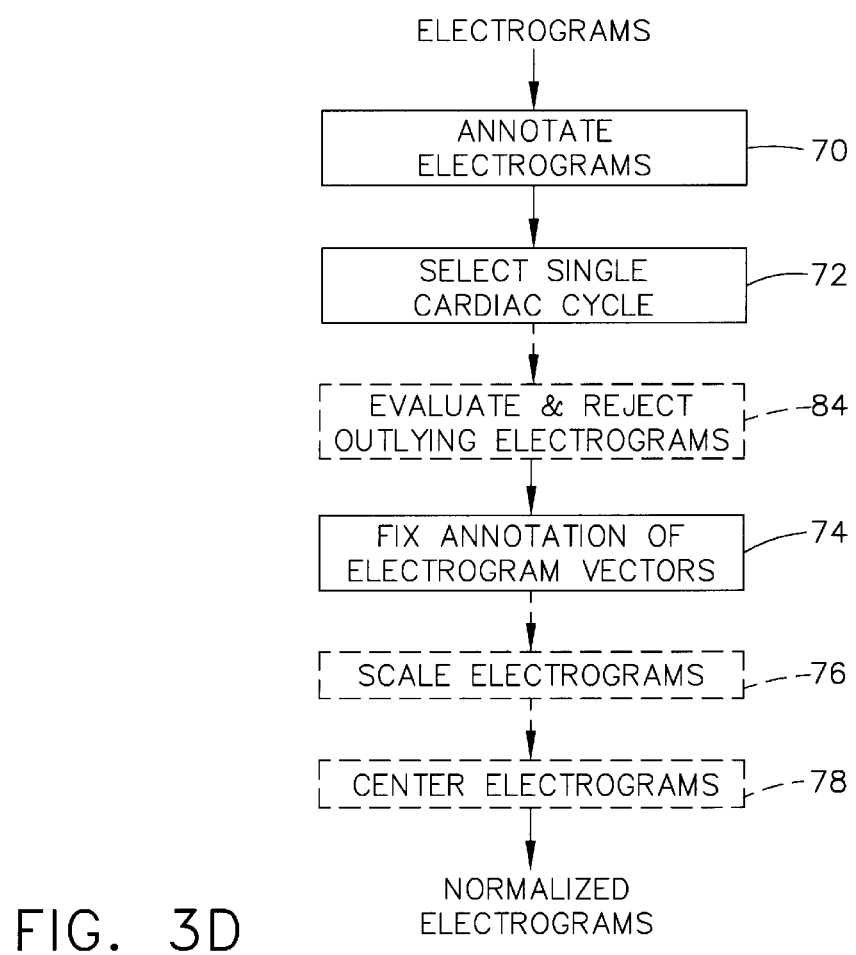
FIG. 3D is a block flow diagram depicting in greater detail the normalizing step of the embodiment of the invention of FIG. 3C.
Figure 3E:
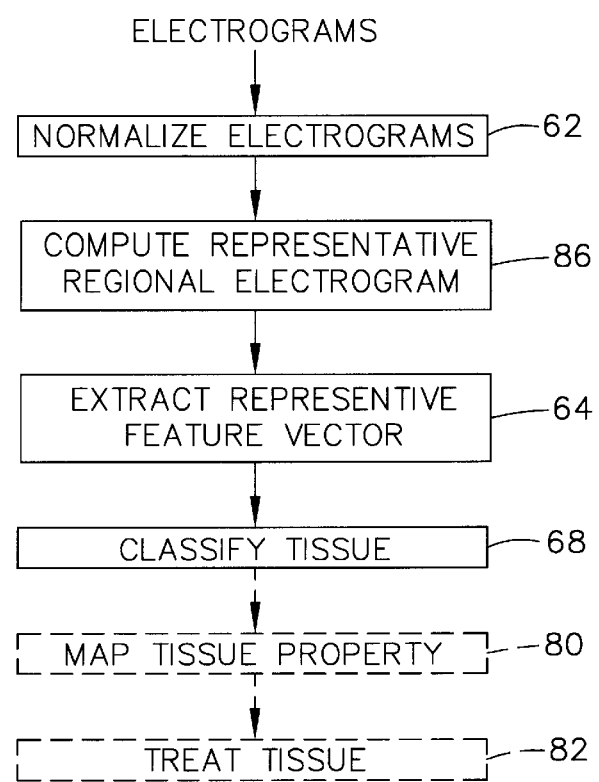
FIG. 3E is a block flow diagram of yet another embodiment of the method of the invention.
Figure 3F:
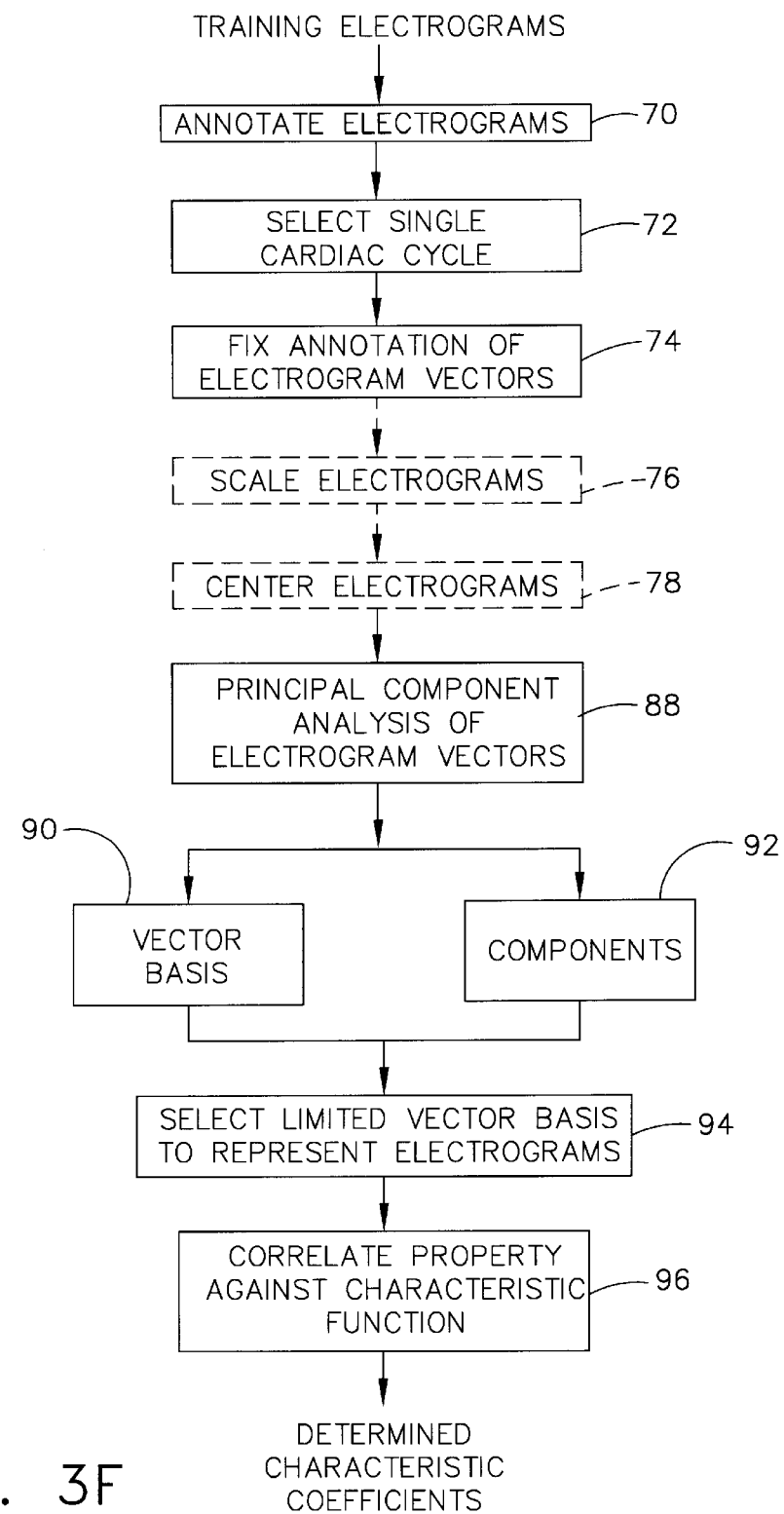
FIG. 3F is a block flow diagram depicting training of a set of electrograms.

Training is effected as shown in FIG. 3F. A set of training electrograms is first annotated 70. A single cardiac cycle is selected from each of the annotated electrograms 72. The position of the annotation is then fixed with respect to each of the electrogram vectors 74 in the training set. The electrograms are then scaled 76 and centered 78. Principal component analysis 88 is then performed on the electrogram vectors to extract a vector basis 90 and a feature vector of components 92. A limited vector basis is selected from vector basis 90 in order to represent the electrograms within a desired error 94. The property to be determined by the method of the invention is then correlated against a characteristic function 96 in order to determine characteristic coefficients that are used as described above.

Let $X_{L \times N} = [x_1, \ldots, x_N]$ be a training set which is a collection of N synchronized, scaled and centered electrograms, each being an L-dimensional column vector:

$$x_n = [x_n^{scc}(t)], t = -L1, \ldots, L2 \; n = 1, \ldots, N$$

The set of electrograms $X_{L \times N}$ on which the training is performed, i.e., the training set, is different than the set of electrograms that is intended for classification.

As disclosed, for example, in Lay D., "Linear Algebra and its Applications" ($2^{nd}$ ed.), Addison-Wesley, 1997, Chap. 7 and in Press W., Teukolsky W., Vettering W. and Flannery B., "Numerical Recipes in C" ($2^{nd}$ ed.), Cambridge University Press, Chap. 2.6, the vector basis $U_{L \times M}$ may be found by means of a technique called Principal Component Analysis (PCA). According to this technique, the desired unitary matrix U is found by means of the singular value decomposition (SVD) of the matrix X. This procedure gives orthogonal matrices U and V and a quasi-diagonal matrix S that satisfies the relationship:

$$X = USV^T = UY$$

In addition to the vector basis U, a matrix $Y_{M \times N} = [y_1, \ldots, y_N]$ is obtained, in which the column $y_n = [y_{1,n}, \ldots, y_{M,n}]^T$ is a component representation of the electrograms $x_n$ (as defined in "Extracting a Feature Vector from the Normalized Electrogram," above). The obtained components $y_{m,n}$ are uncorrelated and in order of decreasing variance. The property of decreasing variance implies that, on average, the lower the component index m, the higher its average contribution to the electrograms. This fact allows us to restrict the number of components to a number M that is much smaller than the original dimensionality L of the electrograms.

The number M is determined as the lowest integer for which the average estimation error is smaller than a given threshold. Knowing the vector basis set $U_{L \times M}$ and each of the components, $y_{m,n}$ for the electrograms in the training set, the original electrograms may be reconstructed as follows:

An estimate $\hat{x}_n^{scc}(t)$ of the scaled and centered electrogram $x_n^{scc}(t)$ can be obtained from its components as:

$$\hat{x}_n^{scc}(t) = \sum_{m=1}^{M} y_{m,n} u_m(t), \; t = -L1, \ldots, L2$$

and thus the estimate $\hat{x}_n^s(t)$ of the original unscaled and uncentered synchronized electrogram $x_n^s(t)$ is given by:

$$\hat{x}_n^s(t) = \alpha_n [\hat{x}_n^{scc}(t) + \bar{x}^s(t)], t = -L1, \ldots, L2$$

wherein $\alpha_n$ and $\bar{x}^s(t)$ are as defined hereinabove. The estimated electrograms $\hat{x}_n^s(t)$ may be compared with the original synchronized electrograms $x_n^s(t)$ in order to obtain an estimation error $e_n$ that expresses the quality of the estimate, given by:

$$e_n = \max_{t=-L1 \ldots L2} |\hat{x}_n^s(t) - x_n^s(t)|, n = 1, \ldots, N$$

The average estimation error may be defined as the arithmetic average of the estimation errors $e_n$, that is:

$$\bar{e} = \frac{1}{N} \sum_{n=1}^{N} e_n$$

The recommended threshold for the average estimation error is 10% of the peak-to-peak amplitude of the average electrogram $\bar{x}^s(t)$.

In order to obtain an appropriate vector basis, the number of electrograms N in the training set should be large. This number of patients from whom electrograms are sampled should be at least about 30, although it is preferred that it be greater than 100. Preferably, about 50 to about 150 electrograms are recorded from each patient. It is most preferred that the database be as large as possible. It is possible to obtain such numbers of electrograms in the training set from a previously prepared database, where data has been taken from a single patient or from many patients under similar conditions (same cardiac regions and similar pathology to that being characterized). It is also possible to constantly update the vector basis by adding new electrograms to the training set as the tissue of new patients is characterized according to the method of the invention.

Computation of Characteristic Coefficients

Given a particular property according to which it is desired to classify the electrograms, it is necessary to have an independent definition of that particular property for every cardiac point from which the electrograms in the training set where recorded. For instance, if the property is the cardiac region to which the electrogram belongs, location information may be made available with the aid of fluoroscopy. If the property is a pathological condition, then the pathological state of the tissue may be obtained from other medical modalities. For example, ischemia may be independently detected with echocardiography, computed tomography (CT), magnetic resonance imaging (MRI) or a nuclear imaging technique such as single photon emission computed tomography (SPECT) or positron emission tomography (PET). The characteristic coefficients, $\alpha_m$, for the given property are determined by performing a search on those coefficients within a limited set of values. The coefficients selected are those that lead to the greatest correlation between the values of the characteristic parameter, $\psi$, and the values of the property as defined by the additional modality.

Another embodiment of the method of the present invention is directed to characterizing the property of cardiac tissue at a plurality of sites in the heart based on a plurality of local electrograms. As shown in FIG. 3C, this embodiment is similar to the embodiment of the invention in which the property is characterized at a single site based on a single local electrogram. In the multi-site embodiment, the steps as defined above for the single local electrogram are repeated for each of the plurality of local electrograms. The resultant characterization of tissue properties at a plurality of sites may be used to construct a map of the tissue property 80 and to treat the tissue 82 based on the mapped property.

As shown in FIG. 3D, the normalization step in the multi-site embodiment of the invention may comprise the optional step of rejecting outlying electrograms 84. The presence of a plurality of electrograms measured at a plurality of sites permits the evaluation of the electrograms and rejection of those that are considered outliers according to one or more criteria. For example, normal electrograms acquired with the catheter of FIG. 1 tend to exhibit minimum values corresponding to maximum depolarization of the underlying tissue. If excessive pressure is applied to the tissue by the catheter tip, the resultant electrograms tend to exhibit minimum values that are shifted to longer times relative to normally acquired electrograms. Thus, when synchronization is performed according to the criterion of minimum value, in normal electrograms, the synchronization point corresponds to the point of maximum depolarization of the corresponding cardiac region. Electrograms with pressure-induced distortion erroneously synchronize at a much later point than the point of normal maximal depolarization. These abnormal electrograms can thus be identified as electrograms that, in order to be synchronized, need to be shifted in time by more than a specific threshold. The recommended value of this threshold for human hearts is about 100 ms.

Another embodiment of the method of the invention is directed at characterizing the property of a region of cardiac tissue based on a plurality of local electrograms acquired in the region. This embodiment of the invention is schematically depicted in FIG. 3E. In this embodiment, electrograms, acquired as enumerated above, are first normalized. A representative electrogram is then computed from the normalized electrograms 86. The representative electrogram may be computed, for example, as the average or the median of all electrograms in the region. The method as described above is then completed using the representative electrogram, i.e., a representative feature vector, which is representative of all of the tissue in the region, is extracted from the representative electrogram. Regional classification of the tissue property is then performed based on the representative feature vector.

Some embodiments of the method of the invention include the step of constructing a map of the property of the heart or the heart chamber characterized according to the method of the invention. A map of the heart based on location information acquired with a catheter position sensor and property information based on local electrograms as described herein may be constructed as described in co-pending commonly assigned U.S. patent application Ser. No. 09/122,137 filed on Jul. 24, 1998 and in its corresponding European Patent Application 974,936 published on Jan. 26, 2000, the disclosures of which are hereby incorporated in their entirety by reference. Briefly, a processor reconstructs a map, preferably a 3-D map, of the cardiac chamber from a plurality of sampled points on the chamber whose position coordinates have been determined. From about five to about fifteen sampled points are generally sufficient in order to perform a preliminary reconstruction of the surface to a satisfactory quality.

An initial, generally arbitrary, closed 3-D curved surface (also referred to herein for brevity as a curve) is defined in a reconstruction space in the volume of the sampled points. The closed curve is roughly adjusted to a shape which resembles a reconstruction of the sampled points. Thereafter, a flexible matching stage is repeatedly performed one or more times in order to bring the closed curve to accurately resemble the shape of the actual volume being reconstructed. The 3-D surface may be rendered to a video display or other screen for viewing by a physician or other user of the map.

The initial closed curved surface preferably encompasses substantially all the sampled points or is interior to substantially all the sampled points. However, it is noted that any curve in the vicinity of the sampled points is suitable. Preferably, the closed 3-D curved surface comprises an ellipsoid, or any other simple closed curve. Alternatively, a non-closed curve may be used, for example, when it is desired to reconstruct a single wall rather than the entire volume.

A grid of a desired density is defined on the curve. For each of the points on the grid, a vector is defined which is dependent on the displacement between one or more of the grid points and one or more of the measured locations on the cardiac surface. The surface is adjusted by moving each of the grid points in response to the respective vector, so that the reconstructed surface is deformed to resemble the actual configuration of the cardiac chamber. The grid preferably divides the curved surface into quadrilaterals or any other polygons such that the grid evenly defines points on the curve. Preferably, the grid density is sufficient such that there are generally more grid points than sampled points in any arbitrary vicinity. Further preferably, the grid density is adjustable according to a desired compromise between reconstruction accuracy and speed.

In preferred embodiments, dedicated graphics hardware, designed to manipulate polygons, is used to perform the reconstruction stages described above.

Preferably, after the geometric map of the chamber is constructed as described above, values of the property determined according to the method of the invention are determined for each of the grid points based on interpolation of the property at surrounding points sampled by the catheter electrode. Thus, the method of the invention results in the generation of a map of a property of the heart chamber as a function of chamber geometry.

Preferably, the property is displayed on the reconstructed surface based on a predefined color scale.

The generated map is generally outputted to a display device such as a computer display or a computer printer.

EXAMPLE

Electrograms were recorded from the left ventricles of 8 dogs at successive stages of ischemia and infarction produced via ligation of the Left Anterior Descending (LAD) coronary artery using a catheter and system as shown in FIG. 1 and FIG. 2. For each dog, mapping was performed at four stages as follows:

1. Baseline (control, prior to ligation)
2. Immediately post ligation (and completed within the 1st hour)
3. 5 hours post ligation
4. 3 days post ligation Mapping consisted of sampling points on the endocardial surface of the left ventricle, such that both the points' location in space and the corresponding electrograms were recorded simultaneously. The electrograms were recorded at every location for a time period of 3 seconds at a sampling rate of 1 KHz. All of the recorded electrograms were annotated and aligned such that all annotations coincide at the $2500^{th}$ sample within the sampled vector. A window between the $2301^{st}$ and $2699^{th}$ samples was taken into account for the database, that is, a window of +200 and −200 ms around the annotation, which includes the last beat. The number of points at which electrograms were acquired in each dog at each stage is shown in

TABLE 1

| Dog Number | Baseline | Immediate | 5 hours | 3 days |
| --- | --- | --- | --- | --- |
| 1 | 76 | 102 | 126 | — |
| 2 | 77 | 125 | 104 | 145 |
| 3 | 90 | 81 | 66 | 159 |
| 4 | 53 | 111 | — | 151 |
| 5 | 107 | 94 | 110 | — |
| 6 | 87 | 79 | 85 | — |
| 7 | 110 | 87 | 99 | 150 |
| 8 | 154 | 133 | 96 | 108 |
| Total Number of Points in Testing Set | 754 | 811 | 686 | 713 |
| Total Number of Points in Training Set | 704 | 714 | 580 | 145 |

Figure 6:
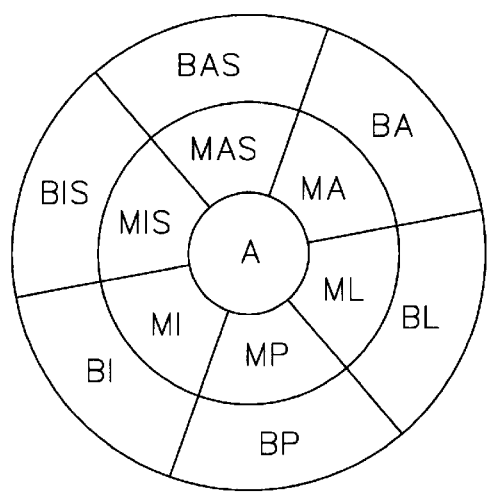
FIG. 6 is a schematic drawing showing regions of the left ventricle of a heart.

The location information of every point in the endocardium was used to group the electrograms according to 13 standard regions. The regions correspond to 6 circumferential zones (anterior, antero-septal, inferior, infero-septal, lateral and posterior) of both the basal and middle sections of the left ventricle, plus one region representing the apex. The locations that were sampled are schematically shown in FIG. 6. The meanings of the codes in FIG. 6 are elaborated in Table 2.

TABLE 2

| Code | Region |
| --- | --- |
| A | Apex |
| MA | Middle anterior |
| MAS | Middle anterior-septal |
| MIS | Middle infero-septal |
| MI | Middle inferior |
| MP | Middle posterior |
| ML | Middle lateral |
| BA | Basal anterior |
| BAS | Basal anterior-septal |
| BIS | Basal infero-septal |
| BI | Basal inferior |
| BP | Basal posterior |
| BL | Basal lateral |

Each region in each map was scored by an experienced echocardiographer according to the degree of contractility. The scores ranged from 1 to 4 wherein, 1 indicates the best contractility and 4 indicates the worst contractility.

Normalization

Since different locations within the heart get activated at different times, the electrograms were annotated and synchronized according to minimum value. A window of L=124 ms to each side of the synchronization point was taken. This resulted in each electrogram being 2L+1=249 samples long.

Training and Testing Data Sets

Since different ischemic stages may be characterized by different signal features, the data sets for each ischemic stage were each treated separately. For every ischemic stage, the testing data set consists of the entire collection of recorded electrograms among all animals that were mapped at that stage, except those that could not be synchronized within a 50 ms window. This condition removed electrograms that exhibited severe ST segment elevation as a result of catheter pressure on the endocardium at the time of the recording. Severe pressure-induced ST segment elevation has been noticed to be usually accompanied by a T segment depression which makes the electrogram erroneously synchronize at this point instead of at the point of normal maximal depolarization.

The training set was defined as the subset from the testing set including only electrograms with normal peak-to-peak amplitude, defined as greater or equal to 15 mV. This choice allowed obtaining comparable training sets and comparable vector bases throughout the different ischemic stages.

Scaling and Centering

In order to emphasize the distinction between electrograms due to differences in morphology, differences in amplitude were compensated for by scaling all the electrograms so that their value at the point of synchronization would equal the value of the average electrogram. In addition, the average of all the synchronized electrograms was removed from each electrogram (electrograms were centered).

Computation of Subspace

The vector basis U was found by means of the singular value decomposition (SVD) of the matrix X, the matrix of electrogram vectors. The obtained components $y_{m,n}$ are uncorrelated and are in order of decreasing variance. Being that the sign of the vectors in the vector basis are arbitrary, the sign was chosen so that the value corresponding to the maximum absolute value of the vector would be positive. This makes graphs easier to visualize. In other words, if $\breve{u}_n(t)$ represents a vector basis element obtained from the SVD algorithm, then the corrected version $u_n(t)$ is given by:

$$u_n(t) = \breve{u}_n(t) \cdot sgn(u_n(t_0)), \quad t=-L, \ldots, L$$

where $$t_0 = \arg\left\{\max_t [abs(u_n(t))]\right\}$$

Figure 7:
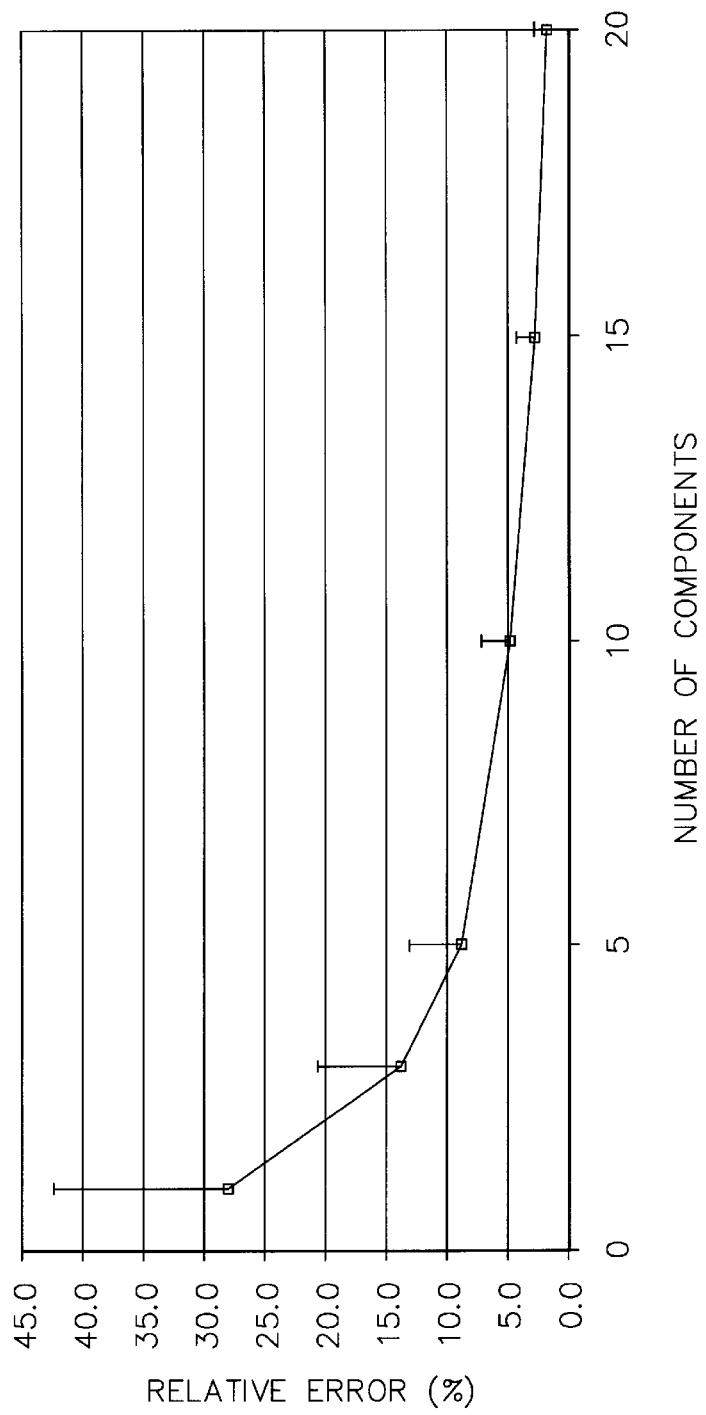
FIG. 7 shows the relative error as a function of number of components for electrograms analyzed in accordance with the method of the invention.

The singular value decomposition produces a vector basis containing M=2L+1 vectors. Since the components are in order of decreasing variance, a much smaller vector basis is needed to represent X with a certain degree of error. It was found that the number of components required to represent electrograms accurately is relatively small. FIG. 7 shows the average approximation error, relative to the average peak-to-peak amplitude, for a representative ischemic stage. It may be observed that no more than 5 components are needed in order to obtain a relative average error of 10% or less.

Extracting Feature Vector from Normalized Electrograms

The transformation U was then applied to the testing set $X'_{L \times N}$, which is the complete set of synchronized and normalized electrograms:

Regional Averaging

The spectrum of principal components was averaged for all the electrograms in the data set that belonged to each one of the 13 myocardial regions, thus obtaining a representative principal component spectrum per region. In other words, single principal components $y_{m,n}$ were replaced by regional averages $\bar{y}_{m,r}$. The echo scores were averaged across dogs as well, thus obtaining a representative echo score per region. The averaging per region is justified by the assumption of homogeneity across dogs. Since the same coronary artery was ligated in all dogs, the pathology is expected to be located in approximately the same regions: apex, mid-anterior and mid-antero-septal.

Correlation with Echo

Single average principal components and linear combinations of them were plotted against average echo scores looking for correlations. In order to reduce the extent of the search, the linear combinations of principal components were limited to the first 5 components and to coefficients, a, of values −1, 0 or 1. The results are summarized in Table 3.

The relatively large error in the correlation is due to the relatively small number of regions taken into account.

TABLE 3

| Ischemic stage | Coefficients | | | | | Correlation with Echo |
|---|---|---|---|---|---|---|
| | $\alpha_1$ | $\alpha_2$ | $\alpha_3$ | $\alpha_4$ | $\alpha_5$ | |
| Immediate | 1 | −1 | 1 | −1 | 0 | 0.77 ± 0.19 |
| 5 hours | 1 | 0 | 0 | 0 | 0 | 0.80 ± 0.18 |
| 3 days | −1 | 0 | −1 | 0 | −1 | 0.84 ± 0.17 |

The $\psi$ parameters described above were computed again for the data recorded at baseline before ligation as a control. The obtained average values per region were compared to the average Echo scores of those regions at the corresponding ischemic stage. This way, if the $\psi$ parameters are indeed only related to pathology, then no correlation should be expected with values obtained with the baseline data. Although a certain degree of correlation was found at baseline for the $\psi$ parameters from the immediate and 5-hour ischemic stages, in all cases the values of the $\psi$ parameters were significantly higher for the pathological regions when pathology was actually present. Even if there was an increase (with respect to baseline) in the values corresponding to the healthy regions, the increase was not as significant as in the pathological regions.

Detection of Ischemia in Individuals

For every individual dog at every ischemic stage, the average value of $\psi$ for points with Echo score of 1 (normal) was compared to the average value of $\psi$ for points with Echo score greater or equal to 3 (scar) by means of a one-tailed t-test. The resultant P-values of t-tests evaluated on $\psi$ parameters between points with Echo=1 and points with Echo≧3 are summarized in Table 4. In some cases, the test could not be performed because of lack of data (either electrical or Echo). In the majority of cases where data was available, characterization of the tissue property (ischemia) from the local electrograms according to the method of the invention was found to be statistically significant.

TABLE 4

| Dog | Immediate | 5 hours | 3 days |
|---|---|---|---|
| 1 | <0.001 | <0.1 | No map |
| 2 | <0.001 | No echo >= 3 | <0.001 |
| 3 | N. S. | No echo | <0.001 |
| 4 | <0.001 | No map | <0.001 |
| 5 | No echo >= 3 | No echo >= 3 | No map |
| 6 | <0.001 | <0.001 | No map |
| 7 | <0.05 | <0.005 | <0.001 |
| 8 | N. S. | <0.001 | <0.001 |

It will be appreciated that the embodiments described above are cited by way of example and the full scope of the invention is limited only by the claims which follow.

What is claimed is:

1. A method of characterizing a property of cardiac tissue at a local site of a heart based of a local electrogram measured at said local site, said method comprising the steps of:
   (a) normalizing said local electrogram, wherein said normalizing comprises;
      (i) annotating said electrogram;
      (ii) selecting a single cardiac cycle from said electrogram; and
      (iii) representing said cardiac cycle of said electrogram as a vector such that said annotation is at a fixed position within said vector;
   (b) extracting a feature vector from said normalized local electrogram; and
   (c) classifying said property of said cardiac tissue at said local site based on said feature vector.

2. A method according to claim 1 wherein said normalizing step further comprises the step of scaling said electrogram.

3. A method according to claim 2 wherein said electrogram is scaled so as to have a fixed value at a feature of said electrogram.

4. A method according to claim 3 wherein said feature corresponds to said annotation.

5. A method according to claim 1 wherein said normalizing step further comprise the step of centering said electrogram.

6. A method according to claim 1 wherein said feature vector is a projection of said normalized electrogram onto a pre-computed subspace.

7. A method according to claim 6 wherein said subspace is computed by principal component analysis of a training set of electrograms.

8. A method according to claim 6 wherein said classifying step is based on the location of said feature vector in said subspace.

9. A method according to claim 1 wherein said property is indicative of the anatomy of said site.

10. A method according to claim 1 wherein said property is indicative of a pathological state said cardiac tissue at said local site.

11. A method according to claim 1 wherein said property comprises the degree of ischemia of said tissue at said local site.

12. A method according to claim 1 which further comprises delivering treatment to said tissue at said local site.

13. A method according to claim 12 which comprises follow-up characterization of the property of said cardiac tissue at said local site to determine the effectiveness of said treatment.

14. A method according to claim 1 wherein said local electrogram is measured with an electrode on a catheter, said catheter further comprising a position sensor, said position sensor measuring the three-dimensional position of said electrode during measurement of said electrogram.

15. A method according to claim 14 wherein said three-dimensional sensor is an electromagnetic sensor.

16. A method of characterizing a property of cardiac tissue at a plurality of local sites of a heart based on a plurality of local electrograms, said method comprising the steps of:
   (a) normalizing said local electrograms, wherein said normalizing comprises:
      (i) annotating said electrograms;
      (ii) selecting single cardiac cycle from each of said electrograms;
      (iii) representing said single cardiac cycle of each of said electrograms as a vector such that said annotation is at a fixed position within said vectors:
   (b) extracting feature vectors from said normalized local electrograms;
   (c) classifying said property of said cardiac tissue at said plurality of local sites based on said feature vectors.

17. A method according to claim 16 wherein said normalizing step further comprises the step of scaling said electrograms.

18. A method according to claim 17 wherein said electrograms are scaled so as to have a fixed value at a feature of said electrograms.

19. A method according to claim 18 wherein said feature corresponds to said annotation.

20. A method according to claim 16 wherein said normalizing step further comprises the step of centering said electrograms.

21. A method according to claim 16 wherein said feature vectors are projections of said normalized electrograms onto a pre-computed subspace.

22. A method according to claim 21 wherein said subspace is computed by principal component analysis of a training set of electrograms.

23. A method according to claim 21 wherein said classifying step is based on the location of said feature vectors in said subspace.

24. A method according to claim 16 wherein said normalization step further comprise rejecting outlying electrograms.

25. A method according to claim 16 wherein said property is indicative of the anatomy of said sites.

26. A method according to claim 25 which further comprises delivering treatment to said tissue.

27. A method according to claim 26 which comprises follow-up characterization of the property of said cardiac tissue to determine the effectiveness of said treatment.

28. A method according to claim 16 wherein said property is indicative of a pathological state said cardiac tissue at said local sites.

29. A method according to claim 16 wherein said property comprises the degree of ischemia of said tissue at said local sites.

30. A method according to claim 16 wherein a plurality of said sites are in a chamber of said heart and wherein said method further comprises constructing a map of said property of said chamber of said heart.

31. A method according to claim 14 wherein said local electrograms are measured with electrode on a catheter, said catheter further comprising a position sensor, said position sensor measuring the three-dimensional position of said electrode during measurement of said electrograms.

32. A method according to claim 31 wherein said three-dimensional sensor is an electromagnetic sensor.

33. A method of characterizing a property of a region of cardiac tissue of a heart based on plurality of local electrograms measured in said region, said method comprising the steps of:
(a) normalizing said local electrograms, wherein said normalizing comprises:
  (i) annotating said electrograms;
  (ii) selecting a single cardiac cycle from each of said electrograms; and
  (iii) representing said cardiac cycle of each of said electrograms as a vector such that said annotation is at a fixed position within said vector;
(b) computing a representative electrogram of said region from said normalized electrograms;
(c) extracting a representative future vector from said representative electrogram;
(d) classifying said property of said cardiac tissue at said region based on said representative feature vector.

34. A method according to claim 33 wherein said normalizing step further comprises the step of scaling said electrograms.

35. A method according to claim 34 wherein said electrograms are scaled so as to have a fixed value at a feature of said electrograms.

36. A method according to claim 35 wherein said feature corresponds to said annotation.

37. A method according to claim 33 wherein said normalizing step further comprises the step of centering said electrograms.

38. A method according to claim 33 wherein said representative feature vector is projection of said representative electrogram onto a pre-computed subspace.

39. A method according to claim 38 wherein said subspace is computed by principal component analysis of a training set of electrograms.

40. A method according to claim 38 wherein said classifying step is based on the location of said representative feature vector in said subspace.

41. A method according to claim 33 wherein said property is indicative of the anatomy of said region.

42. A method according to claim 33 wherein said property is indicative of a pathological state of said cardiac tissue at said region.

43. A method according to claim 33 wherein said property comprises the degree of ischemia of said tissue at said region.

44. A method according to claim 33 wherein said method is repeated for a plurality of regions for said heart.

45. A method according to claim 44 wherein the plurality regions are in a chamber of said heart and wherein said method further comprises constructing a map of said property of said chamber of said heart.

46. A method according to claim 45 which further comprises delivering treatment to said tissue based on said map of said property of said chamber of said heart.

47. A method according to claim 46 which comprises follow-up characterization of the property of said cardiac tissue to determine the effectiveness of said treatment.

48. A method according to claim 33 wherein said local electrograms are measured with electrode on a catheter, said catheter further comprising a position sensor, said position sensor measuring the three-dimensional position of said electrode during measurement of said electrograms.

49. A method according to claim 48 wherein said three-dimensional sensor is an electromagnetic sensor.

50. Apparatus for characterizing a property of cardiac tissue at a local site of a heart based on local electrogram measured at said site, said apparatus comprising:
(a) a catheter; and
(b) a processor having signal processing circuits, the signal processing circuits performing the functions of:
  (i) normalizing said electrogram;
  (ii) extracting a feature vector from said normalized electrogram; and
  (iii) classifying said property of said cardiac tissue at said local site based on said feature vector; and
  (iv) computing a map of said property of said tissue of said heart.

51. Apparatus according to claim 50 wherein the catheter comprises an electrode for measuring said local electrogram, said catheter further comprising a position sensor for measuring the three-dimensional position of said electrode during measurement of said electrogram.

52. Apparatus according to claim 51 wherein said three-dimensional sensor is an electromagnetic sensor.

53. Apparatus according to claim 50 which further comprises means for delivering treatment to said tissue.

* * * * *

UNITED STATES PATENT AND TRADEMARK OFFICE
CERTIFICATE OF CORRECTION

PATENT NO. : 6,725,085 B2
DATED : April 20, 2004
INVENTOR(S) : Armin Schwartzman and Daniel Reisfeld It is certified that error appears in the above-identified patent and that said Letters Patent is hereby corrected as shown below:

<u>Column 18,</u>
Line 14, please delete the word "comprise" and insert therefore -- comprises --
Line 50, after "(ii) selecting" please insert the word -- a --

Signed and Sealed this

Sixth Day of July, 2004

JON W. DUDAS
*Acting Director of the United States Patent and Trademark Office*